United States Patent [19]

Griffiths et al.

[11] Patent Number: 5,612,016
[45] Date of Patent: Mar. 18, 1997

[54] CONJUGATES OF ANTIBODIES AND BIFUNCTIONAL LIGANDS

[75] Inventors: Gary L. Griffiths, Morristown; Habibe Diril, Paterson; Hans J. Hansen, Mystic Island, all of N.J.

[73] Assignee: Immunomedics, Inc., Morris Plains, N.J.

[21] Appl. No.: 38,416

[22] Filed: Mar. 29, 1993

Related U.S. Application Data

[63] Continuation-in-part of Ser. No. 760,466, Sep. 17, 1991, Pat. No. 5,328,679, Ser. No. 581,913, Sep. 13, 1990, abandoned, Ser. No. 518,707, May 7, 1990, abandoned, and Ser. No. 392,280, Aug. 10, 1989, Pat. No. 5,128,119, which is a continuation-in-part of Ser. No. 364,373, Jun. 12, 1989, abandoned, said Ser. No. 760,466, is a continuation-in-part of Ser. No. 408,241, Sep. 18, 1989, abandoned, and Ser. No. 364,373, said Ser. No. 581,913, is a continuation of Ser. No. 176,421, Apr. 1, 1988, Pat. No. 5,061,641, said Ser. No. 518,707, is a continuation-in-part of Ser. No. 176,421.

[51] Int. Cl.$^6$ ............................ A61K 51/10
[52] U.S. Cl. .............. 424/1.49; 424/1.53; 530/391.5; 530/402; 530/408; 530/409; 530/391.3
[58] Field of Search ............... 530/408, 409, 530/402, 391.5, 391.3; 424/1.69, 1.53, 1.49, 1.29

[56] References Cited

U.S. PATENT DOCUMENTS

| | | | |
|---|---|---|---|
| 4,331,647 | 5/1982 | Goldenberg | 424/1 |
| 4,454,106 | 6/1984 | Ganson et al. | 424/1.1 |
| 4,647,655 | 3/1987 | Axén et al. | 530/408 X |
| 4,659,839 | 4/1987 | Nicolotti | 424/9 |
| 4,837,003 | 6/1989 | Nicolotti | 424/1.53 |
| 5,102,990 | 4/1992 | Rhodes | 424/1.49 |
| 5,116,596 | 5/1992 | Bremer et al. | 424/1.53 |
| 5,128,119 | 7/1992 | Griffiths | 424/1.49 |
| 5,134,071 | 7/1992 | Gaetjens | 530/408 X |
| 5,180,816 | 1/1993 | Dean | 424/1.53 X |
| 5,247,075 | 9/1993 | Parker et al. | 424/1.53 X |
| 5,354,554 | 10/1994 | Rhind | 424/1.49 |
| 5,514,363 | 5/1996 | Shochat et al. | 424/1.49 |

*Primary Examiner*—John Kight
*Assistant Examiner*—Lara E. Chapman
*Attorney, Agent, or Firm*—Foley & Lardner

[57] ABSTRACT

Provided are conjugates useful in cancer, cardiovascular or infectious disease detection and/or therapy. The conjugate is of a ligand and protein. The ligand has a moiety capable of binding to mercapto groups and is capable of chelating a metal useful for detection or therapy. The protein reacts with a substance associated with a targeted cell, pathologic lesion or pathogen. The protein prior to conjugation has at least one mercapto group which becomes a site for conjugation to the ligand. Also provided are metal chelates of the conjugate, methods of detection and therapy, methods for producing the conjugate and pharmaceuticals compositions of the conjugates.

16 Claims, No Drawings

CONJUGATES OF ANTIBODIES AND BIFUNCTIONAL LIGANDS

CROSS-REFERENCE TO RELATED APPLICATIONS

This application is a continuation-in-part of Hansen et al., U.S. patent application Ser. No. 07/760,466, filed Sep. 17, 1991, now U.S. Pat. No. 5,328,679, which, in turn, is a continuation-in-part of Hansen et al., U.S. patent application Ser. No. 07/408,241, filed Sep. 18, 1989, now abandoned and Griffiths, U.S. patent application Ser. No. 07/364,373, filed Jun. 12, 1989, now abandoned; is also a continuation-in-part of Shochat et al., U.S. patent application Ser. No. 07/581,913, filed Sep. 13, 1990, now abandoned, and Chang et al., U.S. patent application Ser. No. 07/518,707, filed May 7, 1990, now abandoned, which are, in turn, a continuation and continuation-in-part, respectively, of Shochat et al., U.S. patent application Ser. No. 07/176,421, filed Apr. 1, 1988, now U.S. Pat. No. 5,061,641; and, is also a continuation-in-part of Griffiths, U.S. patent application Ser. No. 07/392,280, filed Aug. 10, 1989, now U.S. Pat. No. 5,128,119, which, in turn, is a continuation-in-part of Ser. No. 07/364,373, filed Jun. 12, 1989, now abandoned; noted above; the disclosures of all of which are incorporated herein in their entireties by reference.

BACKGROUND OF THE INVENTION

1. Field of the Invention

The present invention relates to conjugates of a protein having at least one stereoprotected mercapto group, and a bifunctional ligand capable of coupling to the mercapto group and of chelating with a metal. Specifically, such conjugates are useful for labeling proteins with metals, and can consequently be utilized for the detection and/or therapy of disease states.

2. Description of the Prior Art

Interest in the art of metal chelates and in methods for forming metal chelate-protein conjugates for diagnostic and therapeutic purposes continues. Representative type chelates and conjugates and methods for forming conjugates are disclosed, inter alia, in U.S. Pat. Nos. 4,454,106; 4,472,509; 4,339,426; 4,824,986; 4,831,175; 5,124,471; in EPA 0 279 307 and in German patent 1.155,122. Other proteins including antibodies, monoclonal antibodies and fragments thereof, monoclonal antibodies and fragments thereof which have been structurally altered by recombinant DNA techniques (i.e., chimeric antibodies), polyclonal antibodies, antigens, blood proteins, or proteins bound to blood lymphocytes or other cells can also be employed in the formation of conjugates.

A method for synthesis of bifunctional metal chelates for conjugation to proteins involves reduction of amino acid amides to ethylenediamines to form monosubstituted derivatives which are converted to bifunctional ethylenediaminetetraacetic acid (EDTA) chelates by alkylation with haloacetic acid. (Yeh et al., *Anal. Biochem.* 100:152 (1979)). Similarly, a monosubstituted diethylenetriamine is synthesized by reaction of ethylenediamine with an amino acid ester and reduction of the resulting amide carbonyl. (Brechbiel et al. *Inorg. Chem.* 25:2772–8 (1986)). Alkylation of the diethylenetriamine with haloacetic acid or ester followed by hydrolysis, if applicable, produces a monosubstituted bifunctional diethylenetriamine pentaacetic acid (DTPA) chelate.

Another method of synthesis of a bifunctional DTPA involves reaction of a DTPA or EDTA carboxylate with a chloroformate ester to form a reactive anhydride (Krejcarek et al., *Biochem. Biophys Res. Commun.* 77:581 (1977)). The dianhydride of DTPA used as a bifunctional chelate is prepared by dehydration of the parent DTPA (Hnatowich et al., *Int. J. Appl. Rad. Isot.* 33:327 (1982)). The practice of using an EDTA chelate monosubstituted at the carbon-1 position to better retard the release of metal from chelate in vitro, than the unsubstituted EDTA chelate, has also been reported (Meares et al., *Anal. Biochem.* 142:68 (1984)).

The prior art has formed metal-protein chelate conjugates by mixing monosubstituted bifunctional EDTA or DTPA chelates or DTPA anhydrides with proteins followed by reaction with the metal to be chelated (Krejcarek et al., *Biochem. Biophys. Res. Commun.* 77:581, (1977); Brechbiel et al., *Inorg. Chem.* 25:5783 (1986)). Imaging of tumor target sites in vivo with metal chelate conjugated monoclonal antibodies prepared according to these methods has been reported (Khaw et al., *Science* 209:295, (1980) Sheinberg et al., *Science* 215:151, (1982)). Diagnosis of human cancer in vivo using metal chelate conjugated monoclonal antibody has also been reported (Rainsbury et al., *Lancet* 2:694 (1983)). The use of chimeric antibodies and advantages thereof have been discussed by Morrison, S. L., *Hospital Practice* 24:64–65, 72–74; 77–80 (1989). The potential efficacy of using a hydrolyzable linking group between a chelate and a protein has also been discussed (Paik et al., *J. Nucl, Med.* 30:1693–1701 (1989)).

Disubstituted bifunctional DTPA derivatives have proven useful for labeling of proteins with radioactive metals (Kozak, et al., *Cancer Research* 49:2639–44 (1989)). The introduction of a second substituent on the carbon backbone of DTPA was seen to retard the loss of metal from the DTPA ligand when linked to antibody and injected into the circulation of animals.

The usefulness of radionuclide materials in cancer therapy is disclosed in the article, Kozak et al., "Radionuclide-conjugated monoclonal antibodies: A Synthesis of Immunology, Inorganic Chemistry and Nuclear Science" *Trends in Biotechnology* 4:(10):259–264 (1985). This article discusses the use of antibody conjugates to deliver either alpha or beta radiation. The value of alpha radiation for bismuth-212 in radionuclide therapy is further discussed in the two articles; Kozak et al, "Bismuth-212-labeled anti-Tac monoclonal antibody: Alpha-particle-emitting Radionuclides as Modalities for Radioimmunotherapy," *Proc. Natl. Acad. Sci. U.S.A.* 83:474–478 (1986) and Gansow et al., "Generator-produced Bi-212 Chelated to Chemically Modified Monoclonal Antibody for Use in Radiotherapy," *Am. Chem. Soc. Symposium Series* 15:215–227 (1984). Ligands, for the secure linkage of bismuth to proteins, have not been available (Macklis et al., *Science* 240:1024–2 (1988)).

Examples of other uses for chelated metal ions are disclosed in the following articles. Magerstadt et al., "Gd(DOTA): An alternative to Gd(DPTA) as a $T_1/T_2$ Relaxation Agent for NMR Imaging or Spectroscopy," *Magnetic Resonance in Medicine* 3:808–812 (1986), discloses the usefulness of gadolinium as a relaxation agent for NMR imaging. The article, Spirlet et al., *Inorgan. Chem.* 23:4278–4783(1984), disclosed the usefulness of lanthanide chelates.

All patents and publications referred to herein are hereby incorporated by reference.

However, attempts to employ the tumor localizing properties of metal chelate conjugated monoclonal antibodies for therapeutic purposes have not found common usage because the stability of the radionuclide-linker-antibody conjugate, particularly in vivo over extended time-periods, is of constant concern. This is of special concern when the conjugate is to be used in radioimmunotherapy and contains an alpha- or beta-emitting nuclide. The amount of these highly toxic therapeutic nuclides which can be safely administered is limited by their unwanted dissociation from the antibody-chelate conjugate.

Most therapeutic nuclides are multi-valent heavy metals, and behave physiologically somewhat like iron, a naturally occurring and essential element, noted for its slow absorption into mammalian systems and its virtual negligible excretion, once absorbed. Iron is toxic in high amounts and is never present in circulation in vivo in an uncomplexed form.

The mammalian system goes to great lengths to scavenge free iron and does so by a variety of methods.

One method involves transferrin, an iron transport protein ($K_d$ for $Fe^{3+}>10^{-23}$). Transferrin will (1) transport iron to bone marrow where synthesis of new red blood cells occurs and (2) deposit iron in the storage protein ferritin for future use. Metals which preferentially bind to the anions of "hard acids", which typically containing oxygen ligands, may be susceptible to the transferrin scavenging system. Such metals may include gallium, indium, yttrium, lutetium, scandium, samarium, and gadolinium.

The degree of susceptibility to transchelation to transferrin will vary among metals, depending on other factors such as ionic radius and the precise nature of the structure of the metal-chelate exposed to the challenge of transferrin.

A distinct metal-scavenging system is based on the protein, metallothionein, which is a 7 kD unit having 21 free cysteine residues. The primary function of this protein is heavy metal detoxification, particularly the scavenging of metals which prefer binding to the anions of "soft acids" which are typified by sulfur containing ligands. Such metals may include copper, zinc, cadmium, silver, mercury and lead.

With these two systems (transferrin and metallothionein), mammals are equipped to regulate the bioavailability of potentially toxic heavy metals, thereby protecting themselves against the effects of undesirable elements. While the administration of antibody-chelate linker-radionuclide conjugates containing trace amounts of metals (carrier-free nuclides) is of little concern toxicologically, the design of metal-bearing antibody conjugates must take into account the mammalian defense/metabolism mechanisms outlined above.

It is evident from the above that there continues to be a need for more effective metal chelate protein conjugates that firmly link metals to proteins to minimize metal release and permit highly selective delivery of metals to targeted sites in vivo.

The purpose of this disclosure is to describe improved agents for radioimmunoscintigraphy and particularly radioimmunotherapy, taking the above observations into account.

SUMMARY OF THE INVENTION

In one embodiment, the invention provides a radionuclide which is chelated to a bifunctional ligand conjugated to a protein which binds a marker and which prior to conjugation has at least one stereoprotected mercapto group which becomes a site for is conjugation.

In another embodiment, the invention provides a bifunctional ligand conjugated to an antibody or antibody fragment which prior to conjugation has at least one stereoprotected mercapto group which becomes a site for conjugation. The conjugate contains an antibody or antibody fragment reactive with a tumor-associated antigen.

In another embodiment, the invention provides a bifunctional ligand conjugated to an antibody or antibody fragment which prior to conjugation has been treated to cleave disulfide bonds between the heavy chains to produce free stereoprotected sulfhydryl (mercapto) groups capable of being sites for conjugation.

In another embodiment the invention provides a method for detecting a site of disease. The method comprises parenterally injecting into a human subject having a disease which produces or is associated with an antigen, an amount of a protein which is specific to the antigen and which is conjugated at a stereoprotected sulfhydryl group to a bifunctional chelating agent chelated with a metal capable of detection.

In another embodiment the invention provides a method of therapy of a disease state. The method comprises parenterally injecting into a human subject having a disease which produces or is associated with an antigen, an amount of a protein which is specific to the antigen and which is conjugated at a stereoprotected sulfhydryl group to a bifunctional chelating agent chelated with a therapeutic metal.

In another embodiment, the invention provides a sterile injectable composition comprising a metal chelated to a bifunctional ligand conjugated to a protein which prior to conjugation has at least one stereoprotected mercapto group which becomes a site for conjugation.

In another embodiment, the invention provides a method for preparing a conjugate comprising a bifunctional ligand and a protein from a protein precursor having at least one disulfide linkage. The method comprises (a) reacting a protein precursor with a disulfide reducing agent to form a stereoprotected dimercaptoprotein, and (b) contacting a bifunctional chelating agent with the dimercaptoprotein to form the conjugate.

In another embodiment, the invention provides a method for producing a conjugate comprising an antibody fragment and a bifunctional ligand. The method comprises the steps of:

(a) partially reducing an intact antibody with a reducing agent for cleaving disulfide groups, in an amount sufficient to generate a plurality of proximal free mercapto groups but insufficient to render the antibody immunologically inactive and recovering the partially reduced antibody;

(b) cleaving the partially reduced antibody to generate a reduced F(ab')$_2$ fragment; and (c) contacting a solution of the partially reduced F(ab')$_2$ fragment with a bifunctional chelating agent capable of conjugating to the stereoprotective mercapto groups.

In another embodiment, the invention provides a method for producing a conjugate of a peptide which binds to a marker substance and a bifunctional chelating agent. The method comprises the step of contacting, in solution, a mixture of (a) a peptide containing at least one pendant sulfhydryl group and (b) a bifunctional chelating agent with a reactive group capable of specifically conjugating with the at least one pendant sulfhydryl group wherein the pendant sulfhydryl group is stereoprotected.

DETAILED DESCRIPTION

Compositions and methods are provided related to radionuclides chelated to a bifunctional ligand conjugated with a protein substance, as well as the use of the conjugates for the detection and therapy of lesions, including cancers, infectious diseases, cardiovascular diseases, inflammatory conditions and other pathological conditions.

The cancer states include carcinomas, sarcomas, leukemias, lymphomas, myelomas and neural tumors.

The infectious diseases include those caused by invading microbes or parasites. As used herein, "microbe" denotes virus, bacteria, rickettsia, mycoplasma, protozoa, fungi and like microorganisms; "parasite" denotes infectious, generally microscopic or very small multicellular invertebrates, or ova or juvenile forms thereof, which are susceptible to antibody-induced clearance or lytic or phagocytic destruction, e.g., malarial parasites, spirochetes and the like, including helminths; while "infectious agent" or "pathogen" denotes both microbes and parasites.

The cardiovascular diseases include lesions, such as, vascular clots including thrombi and emboli, myocardial infarctions and other organ infarcts, and atherosclerotic plaques.

A method according to the invention thus broadly comprises the step of contacting a solution of a protein containing a plurality of spatially adjacent stereoprotected free sulfhydryl (mercapto) groups with a solution of bifunctional chelating agent, whereby a solution of a bifunctional chelating agent conjugated to protein at stereoprotected sites is obtained.

A method according to the invention may be used to conjugate a bifunctional chelating agent to other proteins with the requisite free sulfhydryl (mercapto) groups. Proteins which contain one or more proximal free sulflaydryl groups can be labeled directly. Those which contain disulfide groups, normally linked through a cysteine residue, can be treated with a reducing agent to generate the free sulfhydryl groups. Genetic is engineering may be used to produce proteins having free sulfhydryl (mercapto) groups.

The protein substance may be a protein, peptide, polypeptide, glycoprotein, lipoprotein, or the like, e.g. hormones, lymphokines, growth factors, oncogenes and oncogene products, albumin, cytokines, enzymes, immune modulators, receptor proteins, anti-receptor proteins, antibodies and antibody fragments and sub-fragments.

The protein substance will be characterized by either having at least one free stereoprotected mercapto group or at least one accessible disulfide group which upon reduction will provide mercapto groups available as sites for conjugation.

The protein substance of particular interest in the present invention are antibodies and antibody fragments. By "antibodies and antibody fragments" is meant generally immunoglobulins or fragments thereof that specifically bind to antigens to form immune complexes.

The antibody may be whole immunoglobulin of any class, e.g., IgG, IgM, IgA, IgD, IgE, chimetic or hybrid antibodies with dual or multiple antigen or epitope specificities. It can be a polyclonal antibody, preferably an affinity-purified antibody from a human or an appropriate animal, e.g., a primate, goat, rabbit, mouse or the like. Monoclonal antibodies are also suitable for use in the present invention, and are preferred because of their high specificities. They are readily prepared by what are now considered conventional procedures of immunization of mammals with immunogenic antigen preparation, fusion of immune lymph or spleen cells with an immortal myeloma cell line, and isolation of specific hybridoma clones. More unconventional methods of preparing monoclonal antibodies are not excluded, such as interspecies fusions and genetic engineering manipulations of hypervariable regions, since it is primarily the antigen specificity of the antibodies that affects their utility in the present invention. It will be appreciated that newer techniques for production of monoclonals can also be used, e.g., human monoclonals, interspecies monoclonals, chimetic (e.g., human/mouse) monoclonals, genetically engineered antibodies and the like.

Antibody fragments useful in the present invention are those which contain a stereoprotected mercapto group and include F(ab')$_2$, and F(ab)$_2$, and the like including hybrid fragments. Also useful are any subfragments retaining the hypervariable, antigen-binding region of an immunoglobulin and having a stereooprotected mercapto group. This will include genetically engineered and/or recombinant proteins, which incorporate an antigen binding site and otherwise function in vivo as targeting vehicles in substantially the same way as natural immunoglobulin fragments. The fragments may be produced by genetic engineering.

It should be noted that mixtures of antibodies and immunoglobulin classes can be used, as can hybrid antibodies. The hybrids can have two different antigen specificities. Hybrid antibody fragments with dual specificities can be prepared analogously to the anti-tumor marker hybrids disclosed in U.S. Pat. No. 4,361,544. Other techniques for preparing hybrid antibodies are disclosed in, e.g., U.S. Pat. No. 4,474,893 and 4,479,895, and in Milstein et al., *Immunol. Today*, 5,299(1984).

Antibodies against tumor antigens and against pathogens are known. For example, antibodies and antibody fragments which specifically bind markers produced by or associated with tumors or infectious lesions, including viral, bacterial, fungal and parasitic infections, and antigens and products associated with such microorganisms have been disclosed, inter alia, in Hansen et al., U.S. Pat. No. 3,927,193 and Goldenberg U.S. Pat. Nos. 4,331,647, 4,348,376, 4,361,544, 4,468,457, 4,444,744, 4,818,709 and 4,624,846. In particular, antibodies against an antigen, e.g., a gastrointestinal, lung, breast, prostate, ovarian, testicular, brain or lymphatic tumor, a sarcoma or a melanoma, are advantageously used.

Proteins useful for detecting and treating cardiovascular lesions include fibrin-specific proteins, for example, fibringen, soluble fibrin, antifibrin antibodies and fragments, fragment E$_1$ (a 60 kDa fragment of human fibrin made by controlled plasmin digestion of crosslinked fibrin), plasmin (an enzyme in the blood responsible for the dissolution of fresh thrombi), plasminogen activators (e.g., urokinase, streptokinase and tissue plasminogen activator), heparin, and fibronectin (an adhesive plasma glycoprotein of 450 kDa) and platelet-directed proteins, for example, platelets, antiplatelet antibodies and antibody fragments, anti-activated platelet antibodies, and anti-activated-platelet factors, which have been reviewed by Koblik et al., *Semin. Nucl. Med.*, 19:221–237, 1989, all of which is included herein by reference.

A wide variety of monoclonal antibodies against infectious disease agents have been developed, and are summarized in a review by Polin, in Eur. J. Clin. Microbiol., 3(5):387–398, 1984, showing ready availability. These include monoclonal antibodies (MAbs) against pathogens and their antigens such as the following:

Anti-bacterial Mabs

*Streptococcus agalactiae*

*Legionella pneumophilia*

*Streptococcus pyogenes*

*Escherichia coli*

*Neisseria gonorrhosae*
*Neisseria meningitidis*
Pneumococcus
*Hemophilis influenzae B*
*Treponema pallidum*
Lyme disease spirochetes
*Pseudomonas aeruginosa*
*Mycobacterium leprae*
*Brucella abortus*
*Mycobacterium tuberculosis*
*Tetanus toxin*
Anti-viral MAbs
    HIV-1, -2, -3
    Hepatitis A, B, C, D
    Rabies virus
    Influenza virus
    Cytomegalovirus
    Herpes simplex I and II
    Human serum parvo-like virus
    Respiratory syncytial virus
    Varicella-Zoster virus
    Hepatitis B virus
    Measles virus
    Adenovirus
    Human T-cell leukemia viruses
    Epstein-Barr virus
    Murine leukemia virus*
    Mumps virus
    Vesicular stomatitis virus
    Sindbis virus
    Lymphocytic choriomeningitis virus
    Wart virus
    Blue tongue virus
    Sendai virus
    Feline leukemia virus*
    Reo virus
    Polio virus
    Simian virus 40*
    Mouse mammary tumor virus*
    Dengue virus
    Rubella virus
    *=animal virus
Anti-protozoan MAbs
    *Plasmodium falciparum*
    *Plasmodium vivax*
    *Toxoplasma gondii*
    *Trypanosoma rangeli*
    *Trypanosoma cruzi*
    *Trypanosoma rhodesiensei*
    *Trypanosoma brucei*
    *Schistosoma mansoni*
    *Schistosoma japanicum*
    *Babesia bovis*
    *Elmeria tenella*
    *Onchocerca volvulus*
    *Leishmania tropica*
    *Trichinella spiralis*
    theileria parva
    *Taenia hydatigena*
    *Taenia ovis*
    *Taenia saginata*
    *Echinococcus granulosus*
    *Mesocestoides corti*
Antimycoplasmal MAbs
    *Mycoplasma arthritidis*
    *M. hyorhinis*
    *M. orale*
    *M. arginini*
    *Acholeplasma laidlawii*
    *M. salivarium*
    *M. pneumoniae*

Additional examples of MAbs generated against infectious organisms that have been described in the literature are noted below.

MAbs against the gp120 glycoprotein antigen of human immunodeficiency virus 1 (HIV-1) are known, and certain of such antibodies can have an immunoprotective role in humans. See, e.g., Rossi et al., Proc. Natl. Acad. Sci. USA, 86:8055–8058, 1990. Other MAbs against viral antigens and viral induced antigens are also known. This shows that proper selection of the epitope can distinguish between a therapeutic and non-therapeutic target.

MAbs against malaria parasites can be directed against the sporozoite, merozoite, schizont and gametocyte stages. Monoclonal antibodies have been generated against sporozoites (circumsporozoite antigen), and have been shown to neutralize sporozoites in vitro and in rodents (N. Yoshida et al., *Science* 207:71–73, 1980).

Several groups have developed MAbs to T. gondii, the protozoan parasite involved in toxoplasmosis (Kasper et al., *J. Immunol.* 129:1694–1699, 1982; Id., 130:2407–2412, 1983).

MAbs have been developed against schistosomular surface antigens and have been found to act against schistosomulae in vivo or in vitro (Simpson et al., *Parasitology*, 83:163–177, 1981; Smith et al., *Parasitology*, 84:83–91, 1982; Gryzch et al., *J. Immunol.*, 129:2739–2743, 1982; Zodda et al., *J. Immunol.* 129:2326–2328, 1982; Dissous et al., *J. Immunol.*, 129:2232–2234, 1982).

*Trypanosoma cruzi* is the causative agent of Chagas' disease, and is transmitted by blood-sucking reduviid insects. A MAb has been generated that specifically inhibits the differentiation of one form of the parasite to another (epimastigote to trypomastigote stage) in vitro, and which reacts with a cell-surface glycoprotein; however, this antigen is absent from the mammalian (bloodstream) forms of the parasite (Sher et al., *Nature*, 300:639–640, 1982).

Suitable MAbs have been developed against most of the microorganisms (bacteria, viruses, protozoa, parasites) responsible for the majority of infections in humans, and many have been used previously for in vitro diagnostic purposes. These antibodies, and newer MAbs that can be generated by conventional methods, are appropriate for use in the present invention.

Preferred proteins are antibodies or antibody fragments reactive with a tumor associated antigens present on carcinoma or sarcoma cells or lymphomas. Such antibodies are disclosed, e.g., in Goldenberg et al., *Journal of Clinical Oncology*, Vol 9, No. 4, pp. 548–564, 1991 and Pawlak et al., *Cancer Research*, Vol 49, pp. 4568–4577, 1989, as LL-2 and EPB-2, respectively, but which are the same antibody. Others are disclosed in Primus et al. *Cancer Res.*, 43:686–692, 1983, which discloses anti-CEA MAbs; Hansen et al. *Proc. Am. Assoc. Cancer Res.,* 30:414, 1989, which discloses and compares anti-CEA MAbs; Gold et al. *Cancer Res.,* 50:6405–6409, 1990, which disclose MAbs to colon-specific antigen-p (CSAp) and Gold et al. *Proc. Am. Assoc, Cancer Res.,* 31:292, 1990, which disclose an MAb to a pancreatic, tumor-associated epitope.

It has now been found that a protein, in particular, an antibody or antibody fragment, having at least one free sulfhydryl (mercapto) group, can selectively conjugate ligands having a moiety capable of binding to a mercapto group under mild conditions, to form tight bonds to the sulfhydryl group that are quite stable in blood and other bodily fluids and tissues.

Antibodies and some antibody fragments contain one or more disulfide bonds which link the heavy chains, as well as disulfide bonds which join light and heavy chains together. The latter disulfide bonds are normally less accessible to disulfide reducing agents and the bonds linking heavy chains can normally be selectively cleaved. The resultant fragments retain their immunospecificity and ability to bind to antigen. It will be understood that reduction of disulfide bonds linking the heavy chains of an immunoglobulin must be effected with care, since the normally less reactive disulfide bonds linking light and heavy chains will eventually be reduced if reducing conditions are too drastic or the reducing agent is left in contact with the fragments for too long a time.

The reduction of the disulfide bond is advantageously effected with thiol reducing agents, e.g., cysteine, mercaptoethanol, dithioerythritol (DTE), dithiothreitol (DTT), glutathione and the like.

The reduction of the disulfide bonds of the protein, depending on conditions of the reaction, will either (a) only reduce some of the disulfide bonds present thus producing a dimercaptoprotein from the disulfide protein or (b) completely reduce all the disulfide bonds linking the heavy chains and thereby cleave the disulfide protein to produce fragments containing free mercapto sites.

It is preferred that only some of the disulfide bonds present on the protein be reduced thereby producing a dimercaptoprotein in which the mercapto groups are stereoprotected by the tertiary structure of the protein. This results in a conjugate which can better physically protect the metal chelate from transferrin challenge by attaching the chelate to an antibody through one of the antibody's reduced disulfide groups. Since the protein sulfhydryl groups are internal, by virtue of the role of the corresponding disulfide in covalently holding chains together, the ligand is held in a position which is both distant from the antibody binding site and in a less exposed position than the prior art conjugates wherein the ligand was substituted onto a protein lysine residue. The preferred mercapto sites are also stereoprotected in a manner which is not possible by converting a lysine residue to a free thiol by reaction with iminothiolane (Blatter et al. *Biochemistry* 24:1517–1524, 1985), and subsequently attaching the chelate to this non-internal thiol moiety.

In the stereochemically protected position, the corresponding metal-ligand-MAb is located to better withstand the challenge of strong competitive protein chelators, such as transferrin, over an extended time-period. The effect will be to reduce the bone uptake occurring from the transferrin transchelation mechanism discussed above, allowing higher doses of metal to be administered due to lower toxicity, and a better therapeutic response to be achieved. The utility of the approach may be particularly pronounced if agents with longer circulation times such as human MAbs, and isotopes with longer half-lifes are deemed to be better therapy agents.

Reduction of protein containing at least one disulfide bond, for example, an antibody or F(ab')$_2$ fragment, with known disulfide bond reducing agents, e.g., dithiothreitol, cysteine, mercaptoethanol and the like, gives after a short time, typically less than one hour, including purification, antibody having from 1–10 free sulfhydryl (mercapto or thiol) groups by analysis.

Cysteine is preferred for such disulfide reductions and other thiols with similar oxidation potentials to cysteine will also be advantageously used. The ratio of disulfide reducing agent to protein is a function of interchain disulfide bond stabilities and must be optimized for each individual case. Reduction of the disulfide bonds of F(ab')$_2$ antibody fragments is advantageously effected with 10–30 mM cysteine, preferable about 20 mM, and a protein concentration of about 10 mg/ml.

In general, it is advantageous to work with a concentration of antibody or antibody fragment of about 0.01–10 mg per ml, preferably about 0.1–5 mg/ml, of solution, generally in saline, preferably buffered to a mildly acidic pH of about 4.0–4.5.

There are other methods known to those skilled in the art for reducing disulfide groups which are alleged to permit radiolabeling with isotopes, such as technetium and rhenium. Such methods are disclosed in WO 88/07832, published Oct. 6, 1988, U.S. Pat. No. 4,877,868 to Reno at al. and U.S. Pat. No. 5,078,985 to Rhodes, all incorporated herein by reference. While these disclosures are limited to radiolabeling, modifications of the disclosed methods might be useful in the present invention to produce a protein with at least one mercapto group which is stereoprotected.

Once reduced, the protein containing a mercapto group is quite stable if stored lo under rigorously oxygen-free conditions. Stability is also increased with storage at lower pH, particularly below pH 6. A more preferred method of stabilization is to lyophilize the solution of protein containing a mercapto group.

A wide variety or organic chelating agents or ligands can be conjugated to proteins. Organic ligands to be conjugated to proteins may be chosen from among either the natural or synthetic amines, porphyrins, aminocarboxylic acids, iminocarboxylic acids, ethers, thiols, phenols, glycols and alcohols or the polyamines, polyaminocarboxylic acids, polyiminocarboxylic acids, aminopolycarboxylic acids, iminopolycarboxylic acids, nitrilocarboxylic acids, dinitrilopolycarboxlic acids, polynitrilopolycarboxylic acids, ethylenediaminetetracetates, diethylenetriaminepenta or tetraacetates, triethylenetetraamine hexaacetates, polyethers, polythiols, cryptands, polyetherphenolates, polyetherthiols, ethers of thioglycols or alcohols, polyaminephenols, all either acyclid, macrocyclid, cyclic, macrobicyclid or polycyclid, or other similar ligands which produce highly stable metal chelates or cryptates.

A ligand useful in this invention possesses a nonmetal bonded organic functional group suitable for bonding to a mercapto group produced on the protein. Functional groups may be chosen from among bromoacetamides, maleimido or any reactive functional group which is a bimolecular conjugating or coupling agent which binds specifically to a mercapto group in the presence of other functional groups. Other moieties which substantially selectively bind a mercapto group over hydroxy or amino groups are iodoacetyl, chloroacetyl, organo mercurials, alkyl halides, s-triazines, aziridines, epoxides, vinyl sulfones and nitrosoureas under appropriate reaction conditions.

The ligand is preferably a derivative of diethylenetriaminepentaacetic acid (DTPA). It has been found that DTPA ligands tightly bind metal ions and that the DTPA derivative used in this invention forms a chelate conjugated protein that is highly stable, both with respect to the metal chelate binding and with respect to chelate-protein conjugate. These properties are of great importance, particularly for in vivo applications. For example, if the chelate releases the metal ion after introduction into the blood, these ions tend to be bound by transferrin, or the like, and be distributed generally in the circulatory system of the body. Moreover, the ions will ultimately tend to collect and remain in organs such as the liver and spleen, bone or kidney. These effects can have serious consequences depending on the toxicity of the metal and its radioactivity. Furthermore, if the chelate does not form a highly stable conjugate with the antibody, there is a significant reduction in the amount of metal delivered to the target site and a corresponding decrease in efficacy. If the conjugate is used for diagnostic purposes, release of the metal can undesirably increase background radiation. Also, metal chelation to DTPA-protein conjugates is achievable in short time periods in >90% yields, which is a significant utilitarian advantage over ligands with slow metal uptake kinetics.

The metals which may be employed in the present invention may include radioactive or nonradioactive elements with a valency of two or higher. Monovalent metals generally do not form sufficiently stable chelates for the purposes of this invention. Representative radioactive elements may include d-block transition metals, the group IIIA, IVA, VA, VIA, VIIA, IIIB, IVB and VB metals, the lanthanides, actinides and transuranium metals. Nonradioactive metals may be selected, for example, for their useful physical properties such as paramagnetism, fluorescence, or phosphorescence. While this invention is discussed in terms of metals or metal chelates, it will be understood that metal ions are, in fact, chelated in the conjugate.

If the metal chelate conjugated protein is to be used for radioimaging in vivo, a gamma or positron emitting radiometal, such as indium-111 (gamma) or gallium-68 (positron), can be used depending upon the chosen method of detection. For purposes of radiotherapy the radiometals may be an alpha (e.g. bismuth-212, actinium-225 and bismuth-213), a beta (e.g. lead-212, yttrium-90, copper-67, scandium-47) or an Auger electron emitter. An alpha emitter, such as bismuth-212, is desirably employed for therapy. Paramagnetism, fluorescence and phosphorescence can be used, for example, for in vivo or in vitro tests. The choice of any particular metal and valence state is within the skill of the artisan.

Metal chelation is carried out in a solution and, desirably avoids the use of strong acids or bases. Metal chelation for any chelate-antibody conjugate is carried out at a pH which does not significantly reduce the biological activity or specificity of the antibody. Generally, the acceptable range is from about pH 3.2 to about pH 9, however, particular antibodies may have to be restricted to a narrower range. At a pH below 5, adventitious binding of metal ions to antibodies is substantially impaired for many metals. A preferred range, therefore, is often from about pH 3 to about pH 5. Factors peculiar to solutions of the metal employed, however, may permit a pH up to about 9. The selection of the appropriate pH within the range is within the skill of the artisan.

A functionalized DTPA ligand useful in the invention has the structure of Formula I as follows:

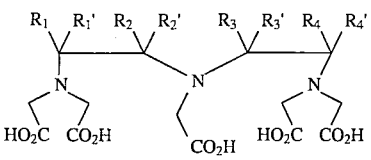

wherein one of $R_1$ or $R_2$ is:

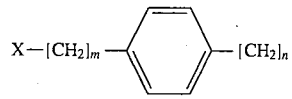

wherein X is a functional group that reacts with a mercapto group in preference to a hydroxy or amino group, preferably is bromoacetimide, maleimido, iodacetyl, chloroacetyl, organo mercurial, alkyl halide, s-triazine, aziridine, epoxide, vinyl sulfone, or nitrosourea, most preferred is bromoacetamide and maleimido; n is 1 to 15, preferably 1–5, most preferably 1; m is 0–15, most preferably 0; $R_1$–$R_4$, $R_1'$–$R_4'$ are independently H or a $C_{1-5}$ alkyl group, or $R_3$ and $R_4$ together form an alkyl chain having 1–6 carbons, referably 4.

The present invention includes the metal chelates of the conjugate of Formula I. Herein, the metals are chosen from the elements including copper, lead, iron, manganese, indium, gadolinium, actinium, lutetium, palladium, chromium, yttrium, scandium, bismuth, the lanthanides, gold, silver, and gallium. Such metal chelates may also be utilized as therapeutic and diagnostic (detection) agents.

Particularly preferred embodiments of the present invention involve metal chelates of the ligand of Formula I with the radioactive isotopes In-111, In-114m, Y-90, Bi-212, Ac-225, Pb-202, Pb-212, Ga-66, Ga-67, Ga-68, Cu-67 and gadolinium.

An additional feature of the bifunctional ligands useful in the invention is that they form stable complexes in vivo with a wide variety of other radiometals of use in cancer detection and therapy. Thus, a patient could be imaged with the In-111 antibody conjugate of the ligand and thereafter treated with the yttrium complex of the same antibody chelate conjugate, thus facilitating calculation of the dose of radioactivity transported to the patient's tumor and so increasing likelihood of the effective application of the therapy.

The metal chelate conjugated antibodies of this invention can be administered in vivo in any suitable pharmaceutical carrier. As noted earlier, a physiologic normal saline solution can appropriately be employed. Often the carrier will include a minor amount of carrier protein such as human serum albumin to stabilize the antibody. The concentration of metal chelate conjugated antibodies within the solution will be a matter of choice. Levels of 0.5 mg per ml are readily attainable but the concentrations may vary considerably depending upon the specifics of any given application. Appropriate concentrations of biologically active materials in a carrier are routinely determined in the art.

The effective dose of radiation or metal content to be utilized for any application will also depend upon the particulars of that application. In treating tumors, for example, the dose will depend, inter alia, upon tumor burden, accessibility and the like. Somewhat similarly, the use of metal chelate conjugated antibodies for diagnostic purposes will depend, inter alia, upon the sensing apparatus employed, the location of the site to be examined and the like. In the event that the patient has circulating antigen in addition to these located at the site, the circulating antigens can be removed prior to treatment. Such removal of antigens can be accomplished, of example, by the use of unlabeled antibodies, or by plasmapheresis in which the patient's serum is treated to removed antigens.

A physiological solution of the protein conjugate is advantageously metered into sterile metal free vials, e.g., at a unit dosage of about 0.1–100 mg protein conjugate/vial, and the vials are either stoppered, sealed and stored at low temperature, or lyophilized, stoppered, sealed and stored. Variations and modifications of these kits will be readily apparent to the ordinary skilled artisan, as a function of the individual needs of the patient or treatment regimen, as well as of variations in the form in which the radioisotopes may be provided or may become available.

Moreover, in a method of detection of or therapy for a cancerous, cardiovascular, infectious or inflammatory lesion, wherein an antibody or antibody fragment which specifically binds to an antigen produced by or associated with the lesion, and conjugated with a bifunctional chelating agent chelated to an effective amount of radionuclide, is parenterally injected into a human patient suffering from lesion, it will represent an improvement to use a radionuclide-bifunctional chelating agent-conjugated antibody or antibody fragment made according to the method of the present invention.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLES

Example 1

1A- Preparation of an Indium/$^{111}$In solution used to determine the chelate to antibody ratio:

Indium foil (226.3 mg) is dissolved in HCl and diluted with H$_2$O to give $1.97 \times 10^3$ mol per 100 ml in 0.6 N HCl. Indium citrate solution is prepared by mixing 5 ul of $1.97 \times 10^{-2}$M InCl$_3$ ($9.85 \times 10^{-8}$ mol) with 94 ul of 0.1M ammonium citrate, pH 5.58 to give $9.85 \times 10^{-4}$M indium citrate after addition of 1 ul of $^{111}$In (13 uCi) in 0.1M ammonium citrate.

1B-Preparation of an $^{111}$In solution:

$^{111}$InCl$_3$ purchased from New England Nuclear, is diluted with 0.1M ammonium citrate, pH 5.58, to give a solution of 15 uCi/ul. This mixture is incubated at room temperature for 1 hour prior to being used for radiolabeling.

Example 2

2A- Reduction of an IgG to IaG-SH

An IgG which is a murine monoclonal antibody against human alpha-fetoprotein (AFP) (Goldenberg et al. *J. Clin. Oncol.* 5:1827–1835, 1987) is reduced with 2-mercaptoethanol (26 mM) at pH 8.7 for 10 minutes at 4° C. to produce IgG-SH. For purification, the reduction mixture is applied to a spin column of Sephadex G-50-80 in 0.1M sodium phosphate, pH 8.1. The number of free stereoprotected SH groups in the effluent is determined by the Ellman reaction (Ellman, *Arch. Biochem. Biophys.* 82:70–77, 1959) to be 4.75 per IgG.

2B-Conjugation of IgG-SH and bifunctional ligand

A conjugation of the IgG-SH with bifunctional ligand is accomplished by incubating a mixture of 450 ul of the IgG-SH (7.3 mg, $4.7 \times 10^{-8}$M) produced as in 2A and 8 ul of bromoacetamidobenzyl-diethylenetriaminepentaacetic acid (Br-Bz-DTPA) ($2.3 \times 10^{-7}$ mol) at 37° C. for 30 min at pH 8.1. The conjugated AFP-IgG-S-Bz-DTPA is purified on a 3 ml spin column of Sephadex G-50-80 in 50/150 mM acetate/NaCl, pH 5.3. The conjugate concentration of the effluent is determined by UV ($\lambda 280$ mm) to be 13.3 mg/ml. The bifunctional ligand to IgG ratio is determined by metal binding assay.

2C-Labeling with the Indium/$^{111}$In solution of 1A to determine DTPA substitution ratio per antibody The conjugate of 2B (5 ul, $4.3 \times 10^{-10}$ mol) is mixed with 5 ul of the $9.85 \times 10^{-4}$M indium citrate ($4.9 \times 10^{-9}$ mol) solution of 1A and 10 ul of 0.1M ammonium citrate, pH 5.58. The mixture is incubated for 70 min at room temperature. ITLC in 10 mM (ethylenediaminetetraacetic acid) shows 36% of the indium is bound to the conjugate. To remove non-specifically bound indium, an aliquot of 1 ul is mixed with a solution of 1 ul of 0.1M EDTA and 8 ul of H$_2$) and incubated for 10 min. Instant Thin-layer Chromatography (ITLC) on silica-gel impregnated glass-fiber strips in 10 mM EDTA (pH 6.4) shows 18% of the $^{111}$In is bound to the conjugate. From this, the chelate to IgG antibody ratio is calculated to be approximately 2.

2D-Labeling with an $^{111}$In solution:

AFP-IgG-S-Bz-DTPA (0.4 ul, 5.3 ug) formed as in 2B, is treated with 40 ul of carrier-free $^{111}$In (726 uCi) in 0.1M ammonium citrate obtained in an analogous manner to the solution of 1B. The radiolabeling mixture is incubated at room temperature overnight. Non-specifically bound $^{111}$In is removed by treatment of the reaction mixture with EDTA (10 mM final concentration) for 10 minutes at room temperature. ITLC of the EDTA chase mixture shows 63% of indium is bound to the antibody.

Purification is achieved on a 3 ml spin column, Sephadex G-50-80,50/150 mM acetate/saline pH 5.3. High Performance Liquid Chromatography (HPLC) of the effluent shows the product elutes at 8.52 minutes on a calibrated size-exclusion column. To ensure complete removal of unbound $^{111}$In, an EDTA chase and ITLC are repeated on an aliquot of the effluent. ITLC shows 99% of the radioactivity remains at the origin, bound to the antibody. Immunoreactivity on anti-AFP affigel is determined to be 73%.

Example 3

3A- Reduction of IgG to IgG-SH:

AFP (IgG) is reduced with 2-mercaptoethanol (10 mM) at pH 8.7 for 10 minutes at 4° C. to produce IgG-SH. For purification, the reduction mixture is applied to a spin column of Sephadex G-50-80 in 0.1M sodium phosphate, pH 8.1. The number of free stereoprotected SH groups in the effluent is determined to be 1.18 per antibody.

3B- Conjugation of IgG and bifunctional ligand

The conjugation of the bifunctional chelator and IgG-SH of 3A is accomplished by incubating a mixture of 450 ul of IgG-SH (5.2 mg, $4.7 \times 10^{-8}$ mol) and 6 ul of bromoacetomidobenzyl-DTPA (Br-Bz-DTPA) ($1.8 \times 10^{-7}$ mol) at 37° C. for 30 min at pH 8.1. The conjugate is purified on an 3 ml spin column of Sephadex G-50-80 in 50/150 mM acetate/NaCl, pH 5.3. The conjugate concentration of the effluent is determined by UV ($\lambda 280$ nm) to be 13.1 mg/ml. The bifunctional ligand antibody ratio is determined by a metal binding assay.

3C- Labeling with the Indium/$^{111}$In solution of 1A to determine DTPA substitution ratio of antibody conjugate The conjugate (5 ul, 4.2×10$^{-10}$ mol) of 3B is mixed with 5 ul of 9.85×10$^{-4}$M indium citrate (4.9×10$^{-9}$ mol) of 1A and 10 ul of 0.1M ammonium citrate, pH 5.58. The mixture is incubated for 70 minutes at room temperature. ITLC in 10mM EDTA shows 18.7% of indium bound to antibody. To remove non-specifically bound indium, an aliquot of 1 ul is mixed with a solution of 1 ul of 0.1M EDTA and 8 ul of H$_2$O and incubated for 10 min. ITLC in 10 mM EDTA (pH 6.4) shows 4.1% of the $^{111}$In is bound to the conjugate. From this, the chelate to antibody ratio is calculated to be 0.48.

3D- Labeling with an $^{111}$In solution

AFP-IgG-S-Bz-DTPA (1.6 ul, 20 ug) of 2B is treated with 40 ul of carrier-free $^{111}$In (680 uCi) in 0.1M ammonium citrate obtained in a manner analogous to 1A. The radiolabeling mixture is incubated at room temperature overnight. Non-specifically bound $^{111}$In is removed by treatment of the reaction mixture with EDTA (10 mM final concentration) for 10 min at room temperature. ITLC in 10 mm EDTA shows 65% of the activity bound to the antibody. Purification is achieved on a 1 ml spin column, Sephadex G-50-80, 50/150 mM acetate/saline, pH 5.3. HPLC of the effluent shows the product eluting at 8.52 min. To ensure complete removal of unbound $^{111}$In, an EDTA chase and ITLC are repeated on an aliquot of the effluent. ITLC shows 99% of the radioactivity at the origin, bound to the antibody. Immunoreactivity on an anti-AFP-affigel is determined to be 81%.

3E- Labeling with another $^{111}$In solution

AFP-IgG-S-Bz-DTPA (52 ul, 777 ug) is treated with 140 ul of $^{111}$In (2.69 mCi) in 0.1M ammonium citrate obtained in a manner analogous to 1B. The radiolabeling mixture is incubated at room temperature for 1 hour. Non-specifically bound $^{111}$In is removed by treatment of the reaction mixture with EDTA (10 mM final concentration) for 10 min at room temperature. ITLC in 10 mM EDTA shows 84% of the activity bound to the antibody.

Purification is achieved on an 1 ml spin column, Sephadex G-50-80, 50/150 mM acetate/saline, pH 5.3. HPLC of the effluent shows the product eluting at 8.59 min. To ensure complete removal of unbound $^{111}$In, an EDTA chase and ITLC are repeated on an aliquot of the effluent. ITLC shows 99.6% of the radioactivity at the origin bound to the antibody. Immunoreactivity on an anti-AFP-affigel is determined to be 97%.

Example 4

A. An IgG which is a murine monoclonal antibody designated LL2 (*J. Clin. Oncol.* 1991), is reduced with a low molecular weight mercaptan, converted to F(ab')$_2$SH by treatment with pepsin and purified by subtraction-chromatography on protein A and by diafiltration. All steps are performed under argon, using solutions that are purged with argon.

B. Conjugation of F(ab')$_2$SH and bifunctional ligand

The conjugation of the bifunctional ligand and F(ab')$_2$-SH of 4A is accomplished by incubating a mixture of 450 ul of F(ab')$_2$-SH (5.2 mg) and 6 ul of bromoacetomidobenzyl-DTPA (Br-Bz-DTPA) (at 5:1 molar excess to F(ab')$_2$) at 37° C. for 30 min at pH 8.1. The conjugate is purified on a 3 ml spin column of Sephadex G-50-80 in 50/150 mM acetate/NaCl, pH 5.3. The conjugate concentration of the effluent is determined by UV ($\lambda$280 nm). The bifunctional ligand/ antibody ratio is determined by a metal binding assay, as described above.

C. Labeling with an $^{111}$In solution

LL2-F(ab')$_2$-S-Bz-DTPA (1.6 ul, 20 ug) of 4B is treated with 40 ul of $^{111}$In (680 uCi) in 0.1M ammonium citrate made in a manner analogous to 1A. The radiolabeling mixture is incubated at room temperatue overnight. Non-specifically bound $^{111}$In is removed by treatment of the reaction mixture with EDTA (10 mM final concentration) for 10 min at room temperature. ITLC in 10 mM EDTA shows amount of activity bound to the antibody. Purification is achieved on a 1 ml spin column, Sephadex G-50-80, 50/150 mM acetate/saline, pH 5.3. HPLC of the effluent shows the product. To ensure complete removal of unbound $^{111}$In, an EDTA chase and ITLC are repeated on an aliquot of the effluent. ITLC shows the radioactivity at the origin, bound to the antibody. Immunoreactivity on affigel is determined.

Example 5—Yttrium-90 Radiolabeling of AFP-IgG-S-Bz-DTPA

AFP-IgG-S-Bz-DTPA (2 ul, 34 ug) in 0.1M sodium acetate buffer, pH 6.5, is added to a solution of yttrium-90 (10 ul, 77 uCi) in 0.5M sodium acetate buffer, pH 6. The solution is mixed and incubated at room temperature for 45 minutes. Instant thin-layer chromatography (ITLC) of an aliquot of the labeling mixture, after incubation, run in 0.01M ethylenediaminetetraacetic acid (EDTA), showed 96.6% of the radioactivity associated with the protein. An aliquot of the labeling mixture is challenged by a 0.01M solution of EDTA for 10 minutes at room temperature to test for non-specifically bound yttrium. ITLC in the same solvent system above shows 96.4% of the yttrium bound to antibody after EDTA challenge.

Example 6—Control Example

6A- Conjugation of IgG and bifunctional ligand

The conjugation of non-reduced AFP (IgG) and bifunctional ligand is attempted by incubating a mixture of 450 ul of IgG (5.2 mg, 4.7×10$^{-8}$ mol) and 6 ul of bromoacetomidobenzyl-DTPA (Br-Bz-DTPA) (1.8×10$^{-7}$ mol) at 37° C. for 30 min at pH 8.1. The conjugate is purified on a 3 ml spin column of Sephadex G-50-80 in 50/150 mM acetate/NaCl, pH 5.3. The conjugate concentration of the effluent is determined by UV ($\lambda$280 nm). The bifunctional ligand/ antibody ratio is determined by a metal binding assay to be 0.04 and 0.06 in two different conjugation experiments, showing lack of conjugate formation in the absence of free thiol groups.

Example 7—Therapy with Product

A subject with suspected disease is injected with an $^{111}$In-IgG conjugate, prepared according to the methodology described above, using an IgG suitably chosen for specificity against the target tissue. At suitable times post-injection (1–336 hours), the subject is imaged with a planar and/or spect imaging system.

Example 8—Therapy with Product

A sample of $^{90}$Y-IgG prepared as described above is diluted and infused into a patient with a disease treated by the IgG in use, at a suitable dose of $^{90}$Y to exert a therapeutic effect with minimal toxicity.

The foregoing examples are merely illustrative and numerous variations and modifications can be effected by one of ordinary skill in the art to adapt the method, kit and uses thereof according to the invention to various usages and conditions without departing from the scope and spirit of the invention.

The broad scope of the invention is defined by the appended claims, and by the myriad of equivalents thereof.

We claim:

1. A precursor conjugate of a therapeutic conjugate, comprising:

(a) an antibody or F(ab')$_2$ antibody fragment having at least one stereoprotected mercapto group, wherein said antibody or F(ab')$_2$ antibody fragment specifically binds to a marker associated with a cancerous lesion or an infectious lesion; and (b) at least one ligand having (i) a first functional moiety which is bound to said stereoprotected mercapto group, and (ii) a chelating functional moiety.

2. The conjugate of claim 1, wherein said antibody is a monoclonal antibody.

3. The conjugate of claim 1, wherein said antibody or antibody fragment specifically binds to an antigen associated with lymphomas, carcinomas, sarcomas, leukemias, myelomas or neural tumors.

4. The conjugate of claim 1, wherein said marker is a viral antigen or viral-induced antigen.

5. The precursor conjugate of claim 1, wherein said first functional moiety of said ligand is selected from the group consisting of bromoacetimide, maleimido, indoacetyl, chloroacetyl, organomercurial, alkyl halide, s-triazine, epoxide, vinyl sulfone and nitrosourea.

6. The conjugate of claim 1 wherein the ligand has a structure of Formula I as follows:

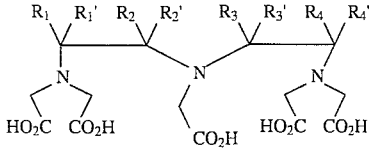

wherein one of $R_1$ or $R_2$ is:

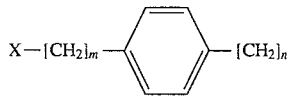

wherein X is a functional group that reacts with a mercapto group in preference to an hydroxy or amino group; n is 1 to 15; Y is $(CH_2)_n$, m is 0–15, and $R_1$–$R_4$, and $R_1'$–$R_4'$ are each independently H or a $C_{1-5}$ alkyl group, or $R_3$ and $R_4$ together form an alkyl chain having 1–6 carbons.

7. The conjugate of claim 6, wherein X is bromoacetamide, maleimido, iodoacetyl, chloroacetyl, organomercurial, alkyl halide, s-triazine, epoxide, vinyl sulfone, or nitrosourea.

8. The conjugate of claim 7, wherein X is bromoacetamide or maleimido.

9. The conjugate of claim 1 wherein the ligand has the structure of Formula I:

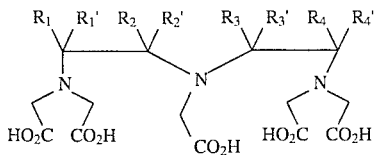

wherein one of $R_1$ or $R_2$ is:

wherein X is bromoacetimide or maleimido; $R_1$–$R_4$, and $R_1'$–$R_4'$, are each independently H or a $C_{1-5}$ alkyl group, or $R_3$ and $R_4$ together form an alkyl chain having 1–6 carbons.

10. A therapeutic conjugate, comprising the precursor conjugate of claim 1, and further comprising yttrium-90 ions chelated to said chelating functional moiety of said ligand.

11. A sterile injectable composition, the composition comprising:

(a) the therapeutic conjugate of claim 10 and (b) a pharmaceutically acceptable injection vehicle.

12. A method of preparing a therapeutic conjugate, wherein said method comprises the step of chelating yttrium-90 ions with said chelating functional moiety of said ligand of the precursor conjugate of claim 1, wherein the product of said chelation step is a therapeutic conjugate for the treatment of a cancerous lesion or an infectious lesion.

13. A method of therapy of an infectious disease which produces or is associated with a marker, the method comprising parenterally injecting into a subject having the infectious disease, a therapeutic amount of a conjugate comprising an antibody or F(ab')$_2$ antibody fragment which specifically binds to said marker and which is conjugated through a stereoprotected cleaved disulfide to a ligand chelated with yttrium-90 ions.

14. A method of cancer therapy, the method comprising parenterally injecting into a human subject having a cancer which produces or is associated with an antigen, a cytotoxic amount of an antibody or F(ab')$_2$ antibody fragment which specifically binds to said antigen and which is conjugated through a cleaved disulfide to a ligand chelated with yttrium-90 ions.

15. The method of claim 14, wherein said antibody or F(ab')$_2$ antibody fragment specifically binds to an antigen associated with lymphomas, carcinomas, sarcomas, leukemias, myelomas or neural tumors.

16. A method for preparing a precursor conjugate of a therapeutic conjugate, comprising the steps of:

(a) partially reducing the disulfide bonds of an antibody or F(ab')$_2$ antibody fragment to produce a dimercaptoprotein having at least one stereoprotected mercapto group, wherein said antibody or F(ab')$_2$ antibody fragment specifically binds to a marker associated with a cancerous lesion or an infectious lesion; and (b) contacting said dimercaptoprotein with a ligand having (i) a first functional moiety which is capable of binding to a mercapto group, and (ii) a chelating functional moiety, wherein said contacting step produces a conjugate of an antibody or F(ab')$_2$ antibody fragment having at least one ligand bound to a stereoprotected mercapto group.

* * * * *